United States Patent [19]

Weaver

[11] Patent Number: 5,571,136
[45] Date of Patent: Nov. 5, 1996

[54] FORCEPS WITH GUIDE WIRE

[75] Inventor: George W. Weaver, East Earl, Pa.

[73] Assignee: Medical Innovations Corporation, Draper, Utah

[21] Appl. No.: 593,541

[22] Filed: Jan. 29, 1996

Related U.S. Application Data

[63] Continuation of Ser. No. 290,142, Aug. 15, 1994, abandoned.
[51] Int. Cl.$^6$ .................................................. A61B 17/00
[52] U.S. Cl. .......................... 606/205; 128/751; 606/174
[58] Field of Search ............................ 606/51, 52, 170, 606/174, 159, 205–210; 128/4, 6, 657, 749–755, 772; 604/22, 96

[56] References Cited

U.S. PATENT DOCUMENTS

| | | | |
|---|---|---|---|
| 3,964,468 | 6/1976 | Schulz | 128/751 |
| 4,953,559 | 9/1990 | Sacerno | 128/751 |
| 5,201,323 | 4/1993 | Vermeulen | 128/749 |
| 5,217,460 | 6/1993 | Knoepfler | 606/52 |
| 5,342,389 | 8/1994 | Haber et al. | 606/205 |

*Primary Examiner*—Michael Powell Buiz
*Assistant Examiner*—William Lewis
*Attorney, Agent, or Firm*—Thorpe, North & Western, L.L.P.

[57] ABSTRACT

Forceps for mounting on a substantially flexible guide wire include a first jaw defining a longitudinal lumen therethrough for mounting of the first jaw on a guide wire and for sliding longitudinal movement of the first jaw along the guide wire. A second jaw is pivotably secured to the first jaw. A flexible longitudinally-extending drive is secured to the second jaw and extends generally parallel to the guide wire. The drive is longitudinally movable between an open position wherein the jaws assume an open orientation enabling tissue to enter therebetween and a closed position wherein the jaws assume a closed orientation such that any tissue which entered intermediate the jaws in the open orientation is grasped therebetween for movement therewith.

9 Claims, 5 Drawing Sheets

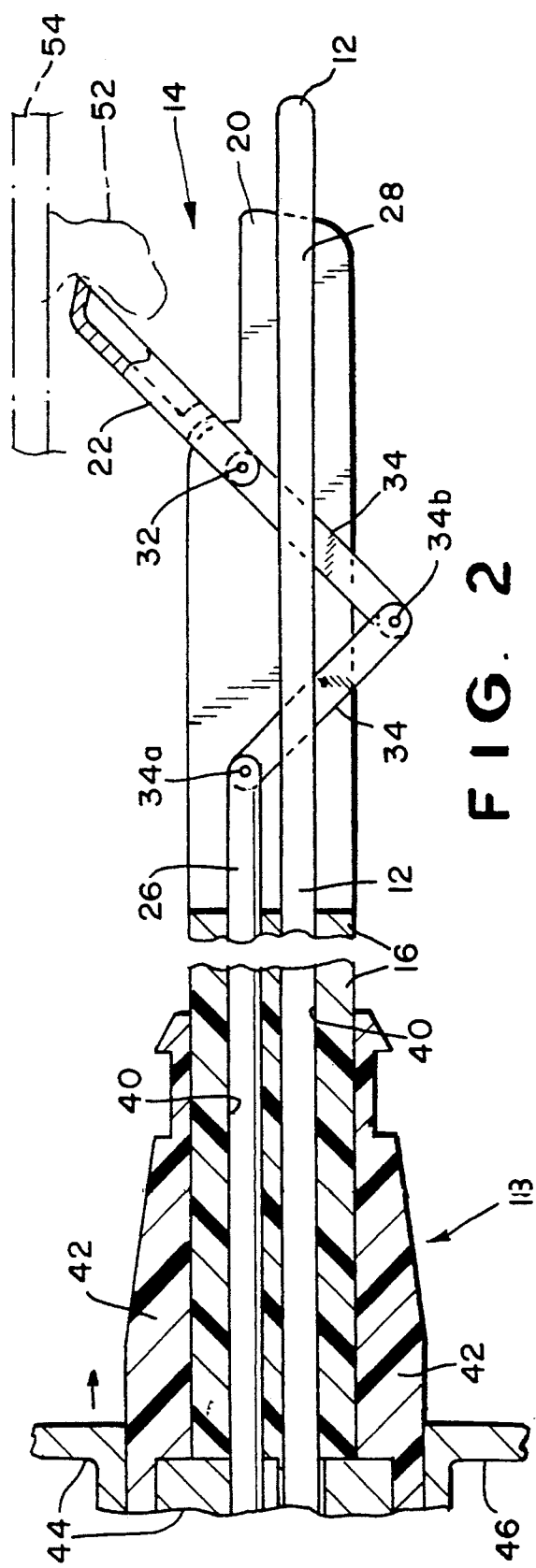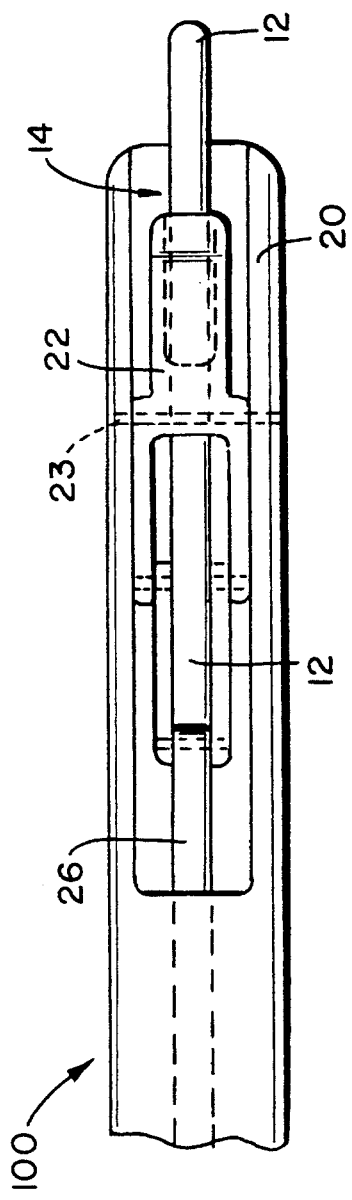

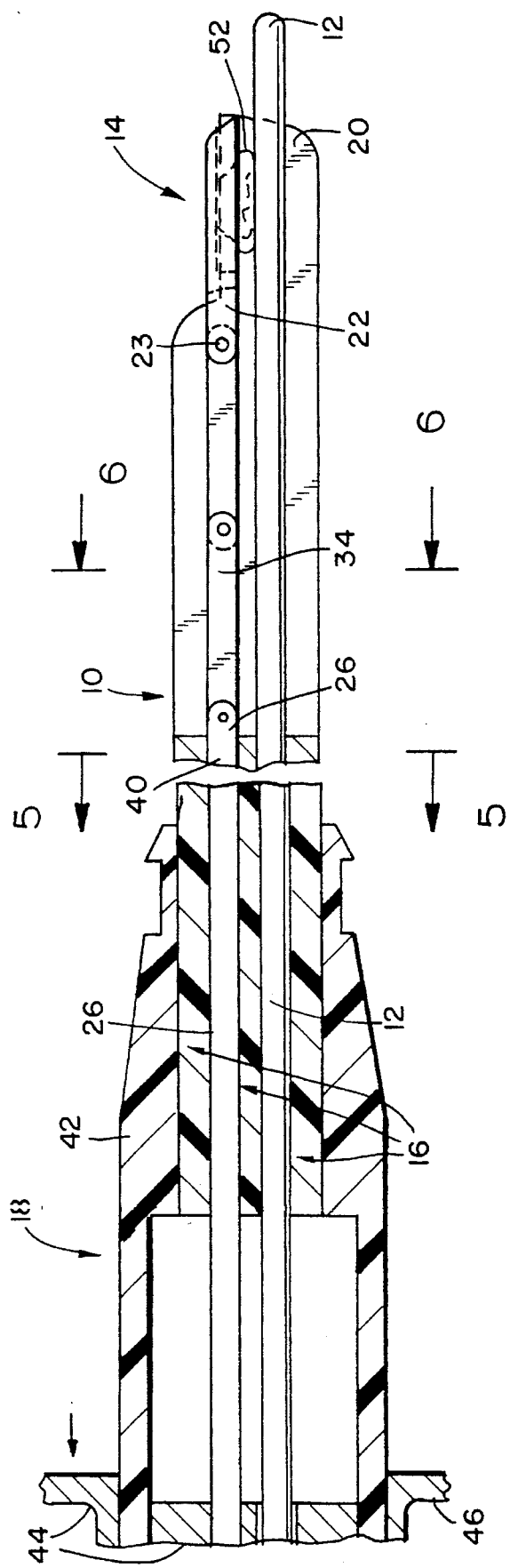

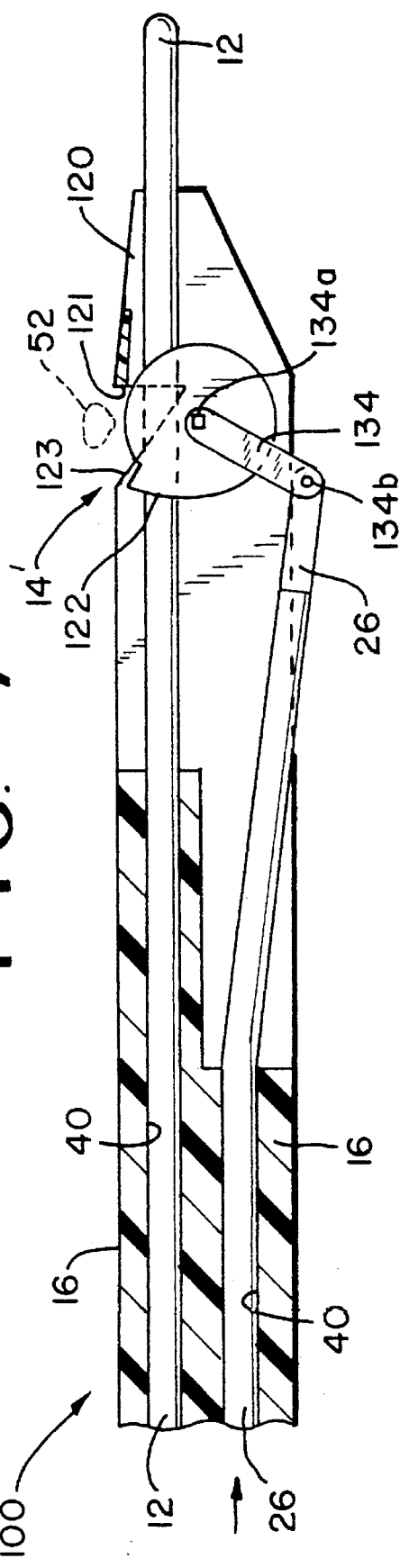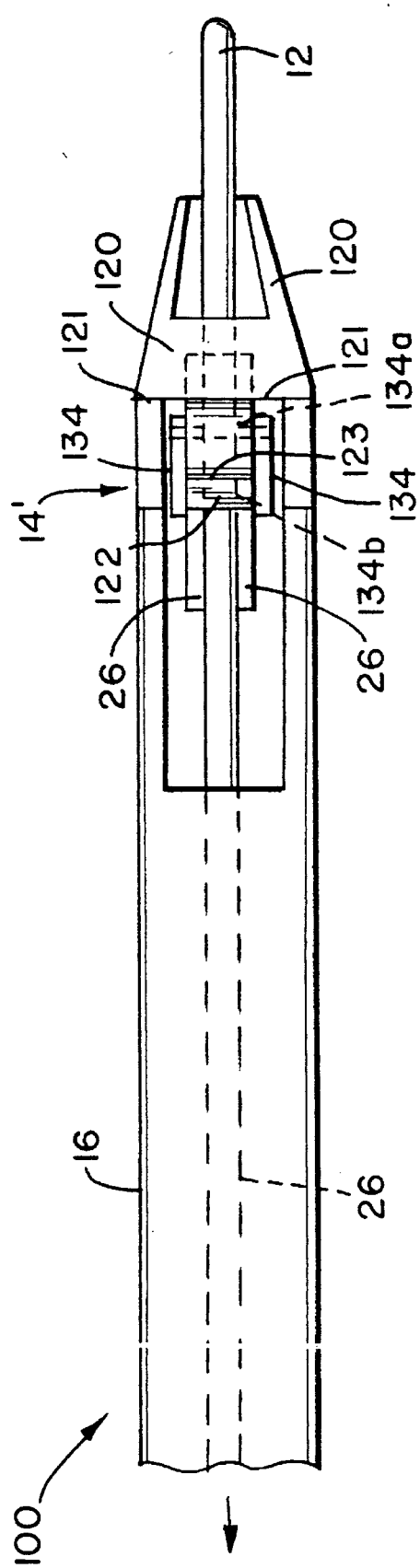

FORCEPS WITH GUIDE WIRE

This is a continuation of application Ser. No. 08/290,142 filed on Aug. 15, 1994, now abandonded.

BACKGROUND OF THE INVENTION

The present invention relates to forceps, and more particularly to forceps for mounting on a flexible guide wire so as to obtain a specimen from the biliary or pancreatic system for Endsoscopic Retrograde Cholangeopancreatography (ERCP) evaluation.

ERCP was originally introduced as a diagnostic radiologic study of the biliary and pancreatic systems that took advantage of endoscopic ampullary access for contrast injection. Today, it is carried out to perform a variety of pancreatico-biliary diagnostic and therapeutic maneuvers. The demand for rapid and accurate ERCP diagnosis has increased, particularly in conditions that involve biliary strictures. It has been reported that the diagnostic sensitivity of a cholangiopancreatogram for pancreatic carcinoma is between 62% to 92%. False positive ERCP studies in diagnosing ductal malignancy, however, may be significant. Of particular concern is mistaken interpretation of biliary strictures, which may arise from benign as well as malignant processes. Thus it is suboptimal to base a therapeutic decision solely on crude, though valuable, ERCP findings. Naturally, this leads to the search for a biliary tissue sampling method that would improve the diagnostic accuracy of cholangiopancreatography.

There are many available methods to sample biliary strictures during ERCP.

(A) CYTOLOGIC METHODS:

Aspiration of obstructed bile fluid

Simple brushing of biliary stricture

Brushing via a "guided" system

Submucosal needle aspiration of obstructive lesion

Stent cytology

Scrape cytology (B) BIOPSY/HISTOLOGIC METHODS:

Forceps biopsy—X-ray guided

Forceps biopsy—cholangioscopically guided

Submucosal needle aspiration biopsy

Scrape biopsy

Each of these methods has its own limitations, restrictions, and difficulties such that no one technique is always preferable to another. Thus, some methods require additional maneuvering after the successful passage of a catheter through the biliary structure, some involve the use of such large caliper instrumentation that there may be some difficulty in passing through tight strictures, some are too harsh and may cause ductal perforation and excessive trauma to the stricture, or perforation of the bile duct. Nonetheless, it is generally considered that forceps biopsy should always be performed because it provides a superior yield of severed tissue compared to other methods. A unique advantage of forceps biopsy over all cytological methods is its ability to identify polyps, fibrosis and other benign tissue changes.

The forceps useful in biliary or pancreatic systems is necessarily substantially flexible. In other words, while the actual tip of the forceps may be substantially rigid (for a length of about 1–2 cm), the remainder of the forceps (which generally extend 200–220 cm) is necessarily highly flexible in order to enable the forceps, once it emerges from the lumen of the endoscope, to follow the tortuous path leading to the biliary duct tree. Nonetheless, great care must be taken during insertion of the forceps to make sure that it travels the desired route or travel path as it is being advanced distally beyond the endoscope. While the intermediate and final positions achieved by the forceps may be determined through x-rays, fluoroscopy, or cholangioscopy for proper execution, the insertion process is necessarily slow and tedious due to the relatively large width of the forceps, typically about 1.8–2.3 mm.

Accordingly, it is an object of the present invention to provide forceps which may be easily and rapidly advanced beyond the endoscope into the biliary tree.

Another object is to provide such forceps which are mounted on a substantially flexible, relatively thin guide wire which has been inserted beyond the endoscope into the biliary tree so that the forceps may be easily and rapidly advanced therealong.

It is a further object to provide such forceps which are easy and economical to manufacture, maintain and use.

SUMMARY OF THE INVENTION

It has now been found that the above and related objects of the present invention are obtained by forceps for mounting on a substantially flexible guide wire. The forceps comprises a first jaw defining a longitudinal lumen therethrough for mounting of the first jaw on a substantially flexible guide wire and for sliding longitudinal movement of the first jaw along the guide wire, and a second jaw pivotably secured to the first jaw for longitudinal movement therewith. Flexible longitudinally-extending drive means are secured to the second jaw and extend generally parallel to the guide wire such that the drive means is longitudinally movable between an open position wherein the jaws assume an open orientation enabling tissue to enter therebetween and a closed position wherein the jaws assume a closed orientation such that any tissue which entered intermediate the jaws in the open orientation is grasped therebetween for movement therewith.

In a preferred embodiment, the first jaw is non-pivotable, and the second jaw is pivotable, longitudinal movement of the drive means causing a pivotal movement of the second jaw. Each of the jaws is generally linear, and the second jaw is secured to the drive means with a coupling pivotable at both ends. Alternately, the second jaw is formed substantially on a radius of a partial cylinder and is secured to the drive means with a coupling pivotable therewith.

The present invention further encompasses an assembly of such forceps and a substantially flexible guide wire passing through the lumen of the first jaw.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein:

FIG. 2 is a fragmentary side elevational view of the assembly with the forceps in the open orientation, a biliary duct and a lesion being illustrated in phantom line;

FIG. 3 is a top elevational view thereof;

FIG. 4 is a view similar to FIG. 2, but showing the closed orientation;

FIGS. 5 and 6 are sectional views taken along the lines 5—5 and 6—6, respectively, of FIG. 4;

FIG. 7 is a side elevational view, partially in cross section, of an assembly according to a second embodiment of the present invention, with the forceps being shown in the open orientation and with a lesion being illustrated in phantom line;

FIG. 8 is a top elevational view thereof;

DETAILED DESCRIPTION OF THE PREFERRED EMBODIMENTS

Figure 1:
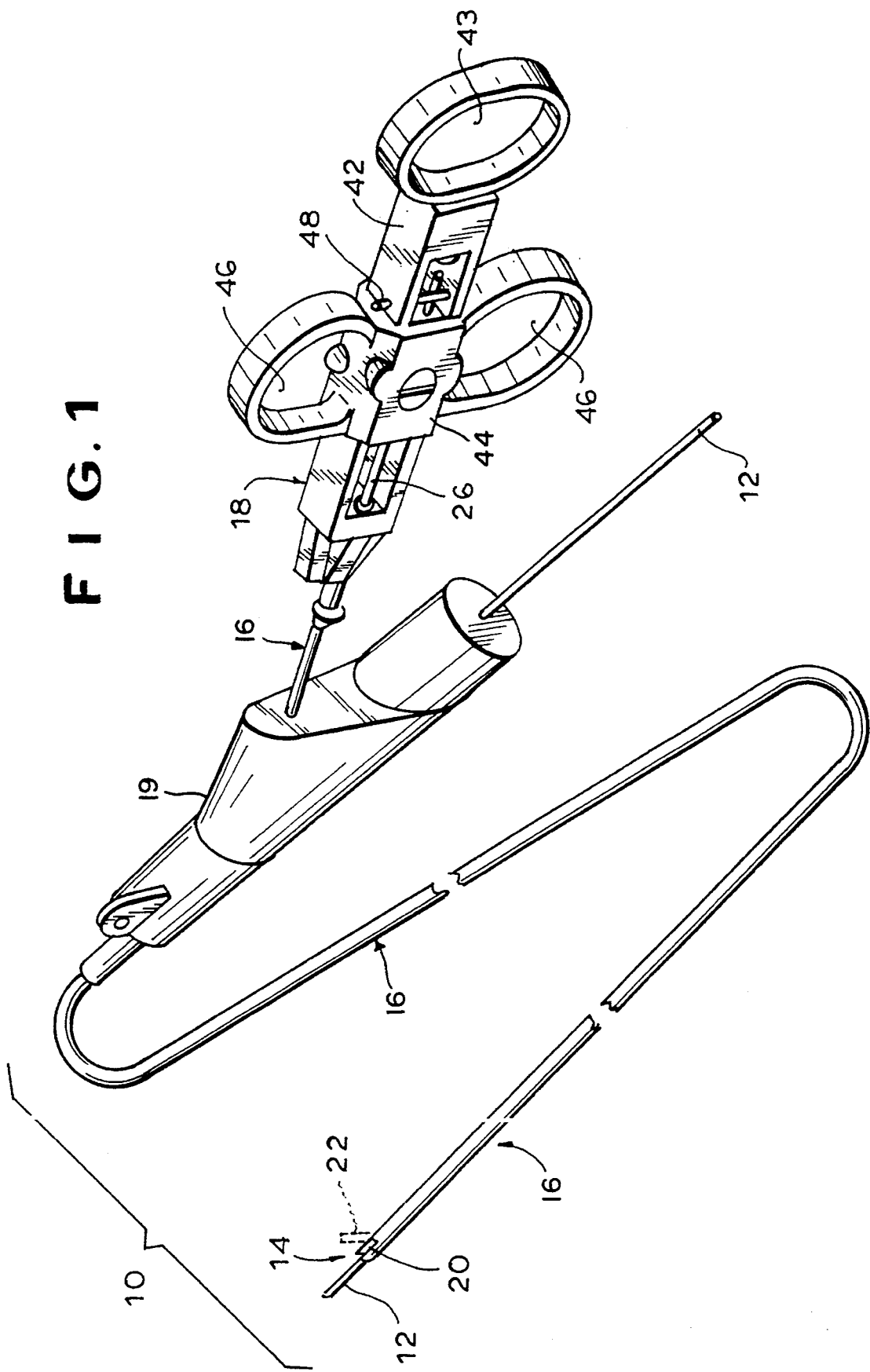
FIG. 1 is a fragmentary isometric view of a biopsy device including an assembly of forceps and a substantially flexible guide wire according to the present invention, with the forceps illustrated in the closed position (and in the open position in phantom line)

Referring now to the drawing, and in particular to FIGS. 1 and 2 thereof, therein illustrated is an assembly according to the present invention, generally designated by the reference numeral 10. The assembly comprises a substantially flexible guide wire 12 (visible distally of the forceps), forceps generally designated 14, a tubular member generally designated 16, and an actuator generally designated 18.

The forceps 14 comprise a non-pivotable rigid jaw 20, a rigid jaw 22 pivotally secured at 23 to the non-pivotable jaw 20, and a flexible longitudinally-extending drive means 26 secured to the pivotal jaw 22 such that the drive means 26 is longitudinally movable between an open position wherein the jaws 20, 22 assume an open orientation (see FIGS. 2 and 3 and in phantom line in FIG. 1) enabling tissue to enter therebetween and a closed position wherein the jaws 20, 22 assume a closed orientation (see FIGS. 1 and 4–6) such that any tissue which enters intermediate the jaws in the open orientation is grasped therebetween for movement therewith. Thus, longitudinal movement of the drive means 26 causes the pivotal movement of the pivotable jaw 22 relative to the non-pivotable jaw 20.

The non-pivotable jaw 20 defines a longitudinally-extending lumen 28 for mounting of the non-pivotable jaw 20 on a guide wire 12 in such a manner as to permit a sliding longitudinal movement of the non-pivotable jaw 20 along the guide wire 12. Preferably the drive means 26 and the guide wire 12 extend generally parallel proximally until the Y-connector 19, where the guide wire 12 continues proximally through one aperture of the connector 19 and the drive means 26 in tubular member 16 continues proximally through another aperture of the connector 19 and into actuator 18. Thus, where the relatively thin guide wire 12 has been pre-inserted through the tubular member 16, it is a simple matter to advance the forceps 14 (including jaws 20, 22 and drive means 26) distally along the guide wire 12 and into the desired final location —e.g., the biliary tree. The sliding of the forceps 14 along the guide wire 12 may be accomplished rapidly and easily as the forceps will at all times follow the guide wire 12 passing through the longitudinal lumen 28 of the non-pivotable jaw 20.

The jaws 20, 22 are preferably formed of stainless steel or a like rigid biocompatible metal and are configured and dimensioned to provide a generous sampling of the tissue to be biopsied. The drive means 26, used in the present invention for moving the pivotable jaw 22 relative to the non-pivotable jaw 20, is substantially similar to that currently in use in biopsy forceps having two movable jaws, except that only one of the linkages (that is, the linkage 34 to the pivotable jaw 22) is required. Disposed within the hollow of drive means 26 is a wire, like the guide wire 12, and both wires 26, 12 fit easily into their respective lumens 40 within tubular member 16, as illustrated in FIG. 5. Both the inner surface of lumens 40 and the outer surface of tubular member 16 are smooth and abrasion-free to facilitate relative longitudinal movement of the guide wire 12 and drive means 26 therethrough as well as passage of the tubular member 16 through the endoscope lumen. Alternatively, one surface may be smooth and the other rough to minimize sliding friction therebetween.

The actuator 18 is provided at the proximal end of the tubular member 16, both to facilitate movement of the forceps 14 to the desired position in the biliary tree and to enable opening and closing of the forceps 14 by the drive means 26. The actuator 18 is conventional in design having a frame 42 with a thumb grip 43 at the proximal end thereof and a reciprocatable member 44 slidingly disposed on the frame 42 and having a pair of finger grips 46. The proximal end of the drive means 26 is secured to the reciprocatable member 44 for movement therewith relative to the frame 42. Where desired, the travel path of the reciprocatable member 44 relative to the frame 42 may be limited by a stop member 48, thereby to prevent over-tightening of the jaws 20, 22 of the forceps 14 on the tissue.

The frame 42 and the thumb grip 43 are used to provide appropriate positioning of the forceps 14 within the biliary tree adjacent to a lesion 46 in a biliary duct 48, while the reciprocatable member 44 and its finger grips 46 are then used to open and close the forceps jaws 20, 22. The jaws 20, 22 assume an open orientation as the reciprocatable member 44 moves the drive means 26 distally to an open position, as illustrated in FIGS. 2 and 3, and a closed orientation as the reciprocatable member 44 moves the drive means 26 proximally to a closed position, as illustrated in FIGS. 4 and 6.

The assembly is introduced into the patient with the reciprocatable member 44 in its proximal position relative to the frame 42 so that the jaws 20, 22 of the forceps 14 are in the closed orientation and thus pass easily through the appropriate lumen of the endoscope. When the forceps 14 have been inserted to an appropriate depth, as determined by x-ray, fluoroscopy, cholangiography or the like, the reciprocatable member 44 is moved distally relative to the frame 42, thereby to cause the drive means 26 to move the movable jaw 22 and thus have the jaws 20, 22 assume an open configuration, as illustrated in FIGS. 2 and 3. A portion of the lesion 52 secured to the biliary duct 54 will enter the opening between the jaws 20, 22. At this point, the retractable member 44 is returned to its original proximal position relative to frame 42, so that the movable jaw 22 closes and the jaws 20, 22 assume the closed configuration, hopefully with a portion of the lesion 52 therebetween, as illustrated in FIGS. 4–6. While the portion of the lesion 52 is illustrated in FIG. 4 as having been separated from the biliary duct 54, in point of fact it may still be attached to the tube and not become severed therefrom until the entire forceps 14 is retracted proximally to tear the portion of the lesion 52 from the biliary duct 54. It will be appreciated that in the embodiment illustrated both jaws 20, 22 are generally linear and that the pivotal jaw 22 is secured to the drive means 26 by a rigid coupling 34 pivotably at both ends 34a, 34b.

Figure 9:
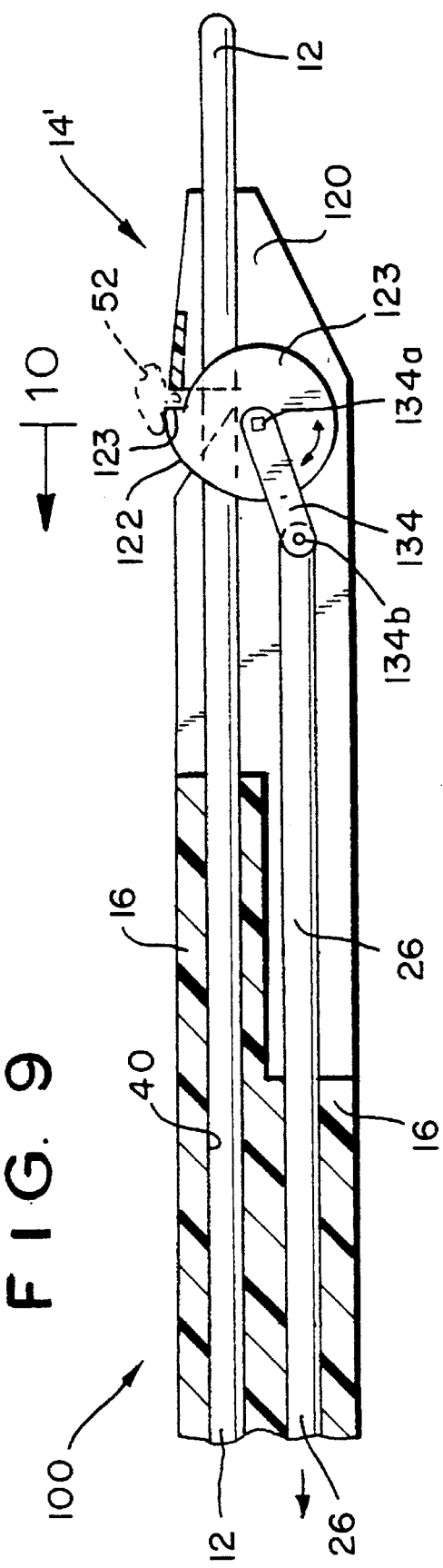
FIG. 9 is a side elevational view similar to FIG. 7, but with the forceps being shown in the closed orientation with a portion of a lesion (illustrated in phantom line) caught between the jaws thereof.
Figure 10:
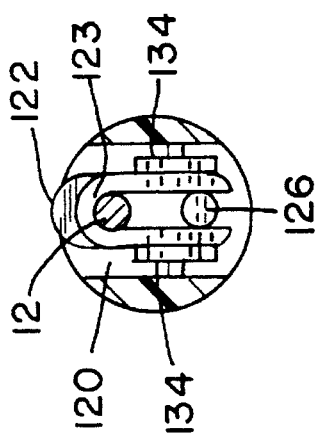
FIG. 10 is a sectional view taken along the line 10—10 of FIG. 9.

Referring now to FIGS. 7–10, therein illustrated is an assembly according to a second embodiment of the present invention, generally designated 100. Elements of like structure and/or function in the first and second embodiments 10, 100 are identified by the same numeral. The second embodiment 100 is similar to the first embodiment 10 except that instead of the jaws 20, 22, there is a fixed jaw 120 having a biting or cutting edge 121 which extends transversely to the guide wire 12 (rather than parallel thereto as in the case of the fixed jaw 20), and the pivotal jaw is a cylinder segment 122 (rather than a linear jaw 22). A segment of the cylinder is removed in order to define a surface 123 for engagement with the surface 121 of fixed jaw 120. The forceps 14' is inserted into the biliary tree with the surfaces 121, 123 of the fixed and movable jaws 120, 122 abutting. Once the forceps 14' is at the desired depth within the biliary tree, the actuator 18 is actuated to move the movable jaw 122 so that the jaws 120, 122 are in the open position and portions of adjacent lesions 52 may enter the opening between surfaces 121, 123, as illustrated in FIGS. 7 and 8. The retractable member 44 of the actuator 18 is then moved distally relative to the frame 42, thereby to cause a proximal movement of the drive means 26. Through the pivotal linkage between the drive means 26 and the coupling end 134b, the coupling 134 is rotated clockwise, thereby also causing a clockwise movement of movable jaw 122. Accordingly, and as shown in FIG. 9, the portion of lesion 52 between the surfaces 121 and 123 of the fixed and pivotal jaws 120, 122 is trapped for removal therewith. Thus the second embodiment 100 differs from the first embodiment 10 in that the coupling 134 is pivotable therewith (i.e., with the jaw 122), rather than being independently pivotable at both ends thereof (as in the case of coupling 34).

The guide wire 12, illustrated in FIGS. 7–10 as positioned above coupling 134, may alternatively be positioned below coupling 134.

To summarize, the present invention provides forceps which may be easily and rapidly advanced beyond the endoscope to the biliary tree because the forceps are mounted on a substantially flexible, relatively thin guide wire which has been inserted beyond the endoscope into the biliary tree so that the forceps may be easily and rapidly advanced therealong. The forceps are easy and economical to manufacture, maintain and use.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. An assembly of forceps and a substantially flexible guide wire, comprising:
    (A) a substantially flexible solid guide wire;
    (B) a non-pivotable rigid jaw defining a longitudinal lumen therethrough, said lumen of said non-pivotable jaw being mounted on said guide wire for sliding longitudinal movement of said non-pivotable jaw along said guide wire;
    (C) a rigid jaw pivotably secured to said non-pivotable jaw; and
    (D) flexible longitudinally-extending drive means secured to said pivotable jaw and extending generally parallel to said guide wire such that said drive means is longitudinally movable between an opening position wherein said jaws assume an open orientation enabling tissue to enter there-between and a closing position wherein said jaws assume a closed orientation such that any tissue which entered intermediate said jaws in said open orientation is grasped therebetween for movement therewith.

2. The assembly of claim 1 wherein longitudinal movement of said drive means causes a pivotal movement of said pivotable jaw.

3. The assembly of claim 1 wherein each of said jaws is generally linear.

4. The assembly of claim 3 wherein said pivotable jaw is secured to said drive means with a coupling pivotable at both ends and at a point between said ends, one of said coupling ends being secured to said drive means for movement therewith and the other of said coupling ends being secured to said pivotable jaw for movement therewith.

5. The assembly of claim 1 wherein said pivotable jaw is formed substantially on a radius of a partial circle.

6. The assembly of claim 5 wherein said pivotable jaw is secured to said drive means with a rigid coupling pivotable at both ends thereof, one of said coupling ends being secured to said drive means for movement therewith, and the other of said coupling ends being secured to said pivotal jaw for movement therewith.

7. The assembly of claim 5 wherein said pivotable jaw is pivotably secured to said drive means with a coupling pivotable therewith.

8. An assembly of forceps and a substantially flexible guide wire, comprising:
    (A) a substantially flexible guide wire;
    (B) a non-pivotable rigid jaw defining a longitudinal lumen therethrough, said lumen of said non-pivotable jaw being mounted on said guide wire for sliding longitudinal movement of said non-pivotable jaw along said guide wire;
    (C) a rigid jaw pivotably secured to said non-pivotable jaw;
    (D) flexible longitudinally-extending drive means secured to said pivotable jaw and extending generally parallel to said guide wire such that said drive means is longitudinally movable between an opening position wherein said jaws assume an open orientation enabling tissue to enter therebetween and a closing position wherein said jaws assume a closed orientation such that any tissue which entered intermediate said jaws in said open orientation is grasped therebetween for movement therewith; and
    (E) a coupling securing said pivotable jaw and said drive means together, said coupling being pivotable at both ends and at a point between said ends, one of said coupling ends being secured to said drive means for movement therewith and the other of said coupling ends being secured to said pivotable jaw for movement therewith.

9. An assembly of forceps and a substantially flexible guide wire, comprising:
    (A) a substantially flexible guide wire;
    (B) a non-pivotable rigid jaw defining a longitudinal lumen therethrough, said lumen of said non-pivotable jaw being mounted on said guide wire for sliding longitudinal movement of said non-pivotable jaw along said guide wire;
    (C) a rigid jaw pivotably secured to said non-pivotable jaw; and
    (D) flexible longitudinally-extending drive means secured to said pivotable jaw and extending generally parallel to said guide wire such that said drive means is longitudinally movable between an opening position wherein said jaws assume an open orientation enabling tissue to enter therebetween and a closing position wherein said jaws assume a closed orientation such that any tissue which entered intermediate said jaws in said open orientation is grasped therebetween for movement therewith; and (E) a coupling securing said pivotable jaw and said drive means together, said coupling being rigid and pivotable at both ends thereof, one of said coupling ends being secured to said drive means for movement therewith, and the other of said coupling ends being secured to said pivotable jaw for movement therewith.

\* \* \* \* \*